US00PP29139P3

(12) United States Plant Patent
Ammerlaan

(10) Patent No.: US PP29,139 P3
(45) Date of Patent: Mar. 20, 2018

(54) ***ASTROLOBA* PLANT NAMED 'OVASDINO'**

(50) Latin Name: *Astroloba spiralis*
Varietal Denomination: OVASDINO

(71) Applicant: Johannes Hendrikus Adrianus Ammerlaan, Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 15/530,592

(22) Filed: Feb. 3, 2017

(65) Prior Publication Data

US 2017/0257995 P1 Sep. 7, 2017

(30) Foreign Application Priority Data

Mar. 3, 2016 (QZ) ..... PBR 2016/0663

(51) Int. Cl.
*A01H 5/00* (2006.01)
*A01H 5/12* (2018.01)

(52) U.S. Cl.
USPC ..... Plt./373
CPC ..... *A01H 5/12* (2013.01)

(58) Field of Classification Search
USPC ..... Plt./373, 372
CPC ..... A01H 5/12; A01H 5/02; A01H 5/00
See application file for complete search history.

*Primary Examiner* — Kent L Bell
(74) *Attorney, Agent, or Firm* — Samuel R. McCoy, Jr.

(57) ABSTRACT

A new and distinct *Astroloba spiralis* cultivar named 'OVASDINO' which is characterized by a large plant size, foliage arranged in a single non-branched basal rosette that forms a short stem with time, large dark green leaves which are spotted with light green papillae, dentate leaf margins with relatively large spines, as well as the stability of these characteristics from generation to generation.

4 Drawing Sheets

Latin name of the genus and species: The Latin name of the genus and species of the novel variety disclosed herein is *Astroloba spiralis.*

Variety denomination: The inventive variety of *Astroloba* disclosed herein has been given the variety denomination 'OVASDINO'.

CROSS REFERENCE TO RELATED APPLICATIONS

This application claims priority to the Community Plant Variety Rights application number 2016/0663, filed Mar. 3, 2016, which is herein incorporated by reference.

BACKGROUND OF THE INVENTION

Parentage: 'OVASDINO' originated as a naturally occurring, whole-plant mutation of the species *Astroloba spiralis* (not a named variety or cultivar). In 2010 the inventor discovered the mutation at a commercial greenhouse in Bleiswijk, The Netherlands, growing amongst a crop of the species *Astroloba spiralis.* The mutation was noted for its unique growth habit and foliage coloration. The mutation was asexually propagated by leaf cuttings in order to confirm the distinctness and stability of the characteristics first observed. After further evaluation it was determined that the unique characteristics of the candidate plant would prove favorable for commercial marketability. The new variety was given the breeder denomination 'OVASDINO'.

Asexual Reproduction: Asexual reproduction of the new cultivar 'OVASDINO', by way of rooting leaf cuttings, was first initiated in the summer of 2015 at the inventor's commercial greenhouse in Bleiswijk, The Netherlands.

Through eight subsequent generations, the unique features of this cultivar have proven to be stable and true to type.

SUMMARY OF THE INVENTION

The cultivar 'OVASDINO' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVASDINO'. These characteristics in combination distinguish 'OVASDINO' as a new and distinct *Astroloba spiralis* cultivar:

1. 'OVASDINO' exhibits a large plant size with foliage arranged in a single non-branched basal rosette, forming a short stem with time; and
2. 'OVASDINO' exhibits large, dark green leaves which are lightly covered with light green papillae on the adaxial leaf surface and moderately to heavily covered with light green papillae on the abaxial leaf surface; and
3. 'OVASDINO' exhibits dentate leaf margins with relatively large spines.

BOTANICAL DESCRIPTION OF THE PLANT

Figure 1:
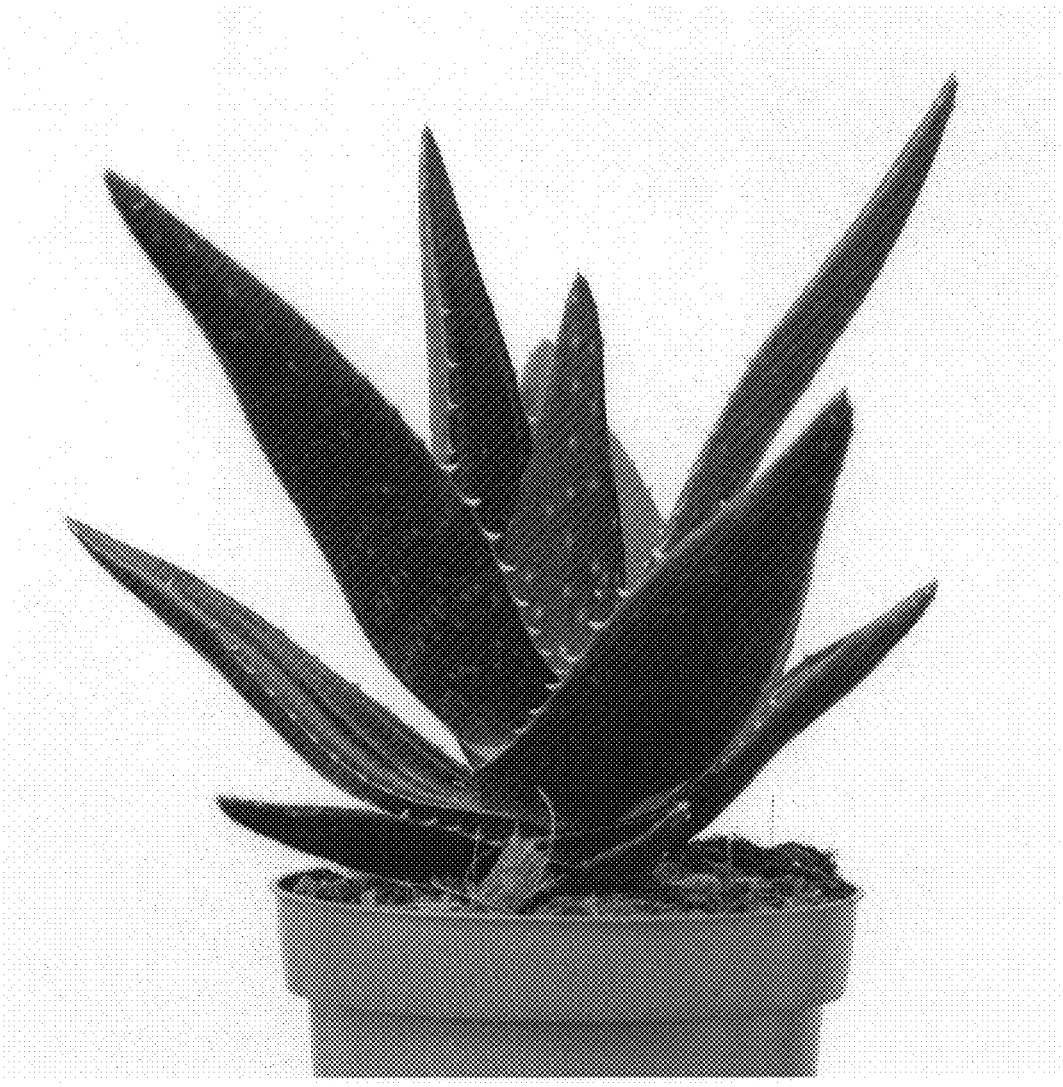
FIG. 1 illustrates, as nearly true as it is reasonably possible to make the same in color photographs of this type, an exemplary plant of 'OVASDINO' grown in a commercial greenhouse in Heerhugowaard, The Netherlands. This plant is approximately 8 months old, shown planted in a 12 cm container.
Figure 2:
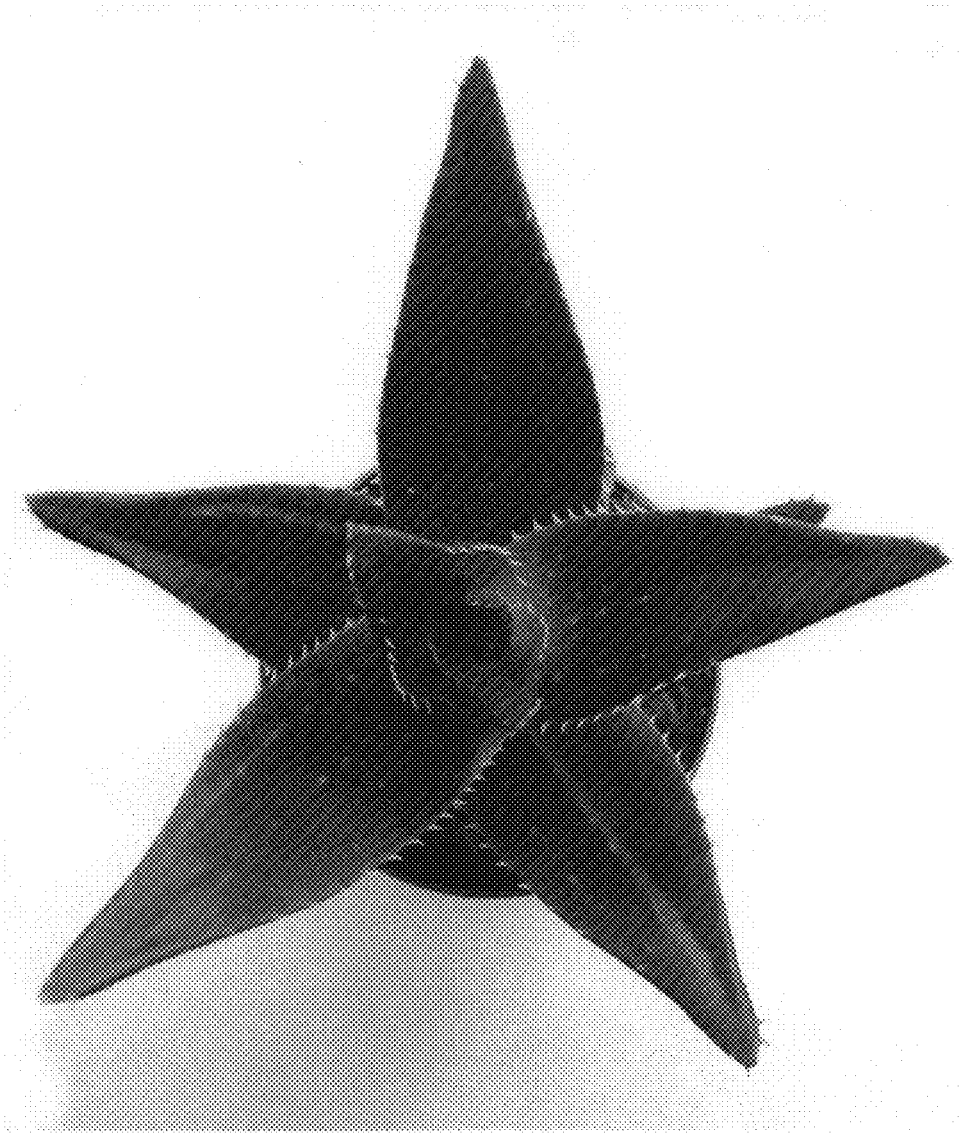
FIG. 2 illustrates, as nearly true as it is reasonably possible to make the same in color photographs of this type, the typical foliage arrangement of 'OVASDINO'.
Figure 3:
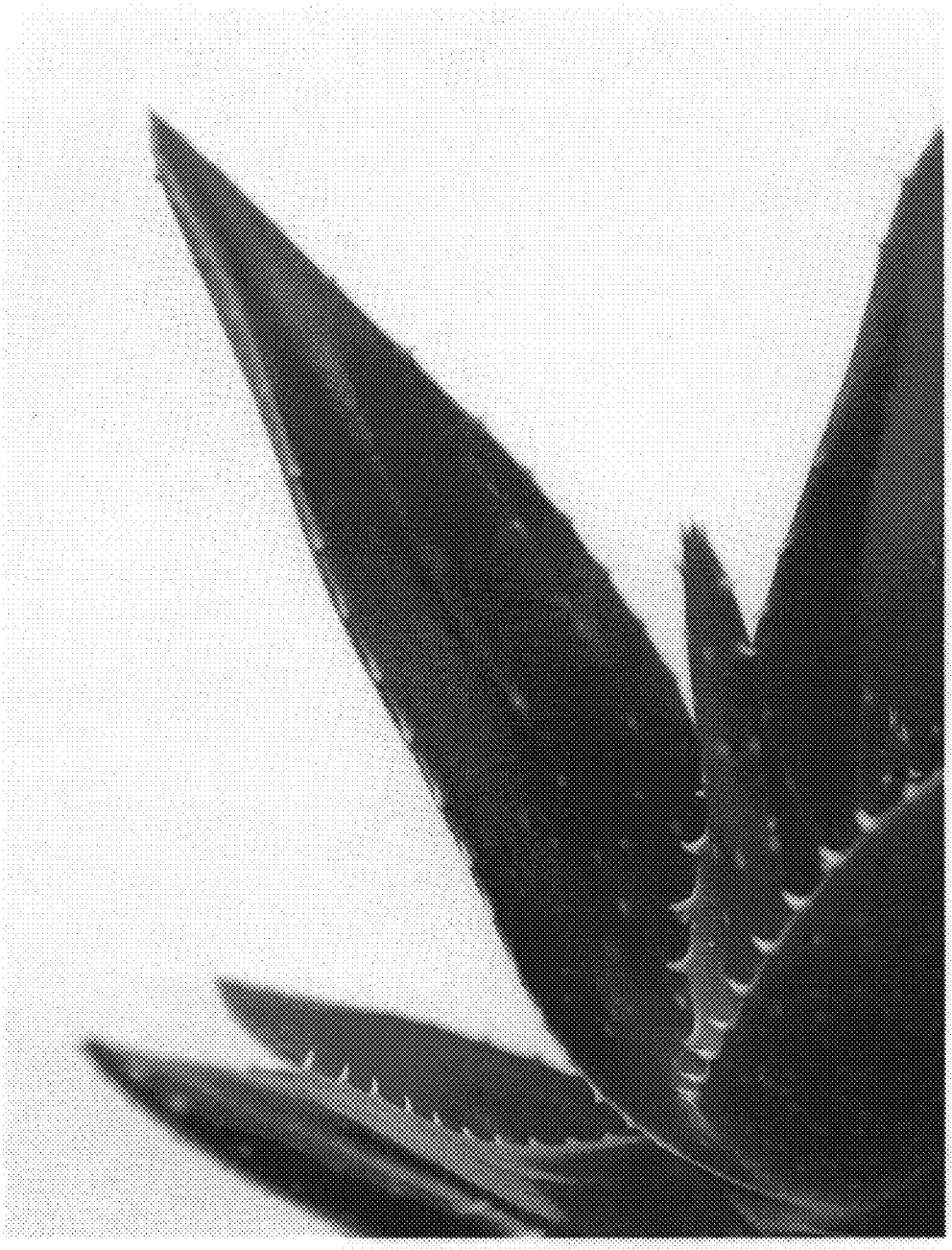
FIG. 3 illustrates, as nearly true as it is reasonably possible to make the same in color photographs of this type, the adaxial surface of the mature foliage 'OVASDINO'.
Figure 4:
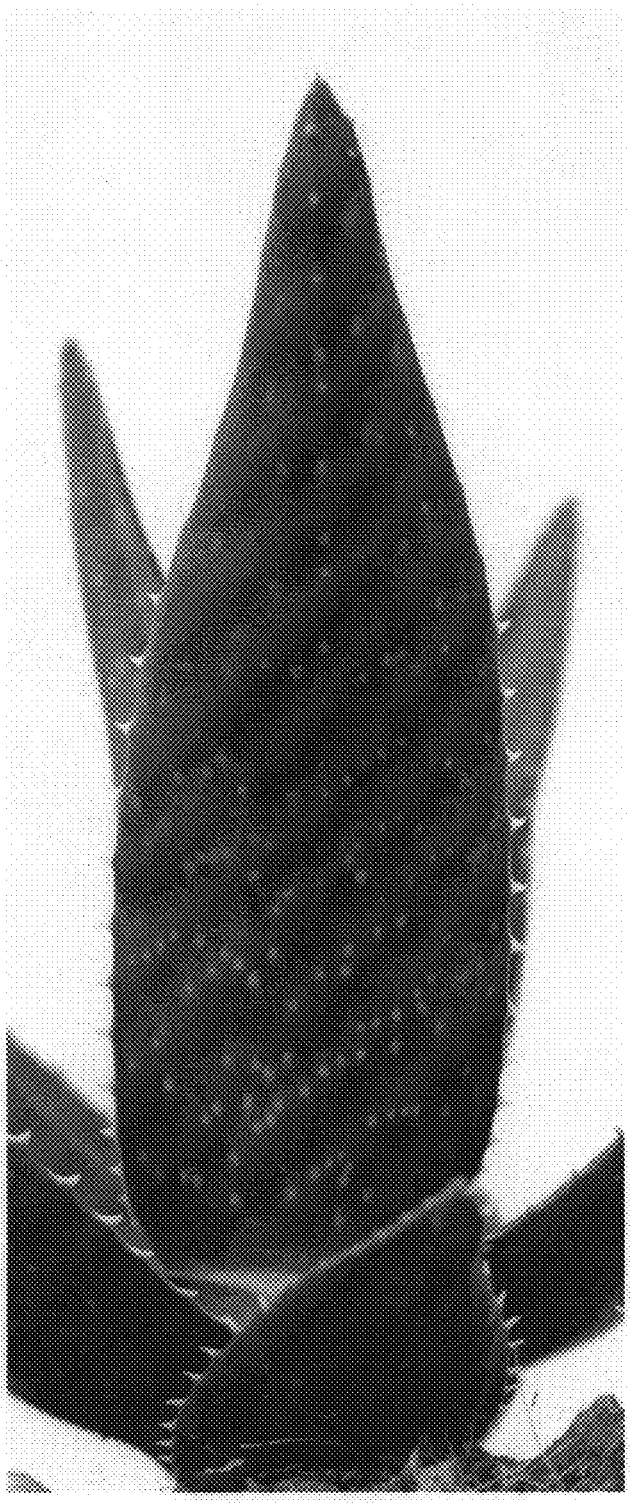
FIG. 4 illustrates, as nearly true as it is reasonably possible to make the same in color photographs of this type, the abaxial surface of the mature foliage 'OVASDINO'.

The following observations and measurements made in January of 2017 describe averages from a sample set of six specimens of 8 months old 'OVASDINO' plants grown in 12 cm nursery containers at commercial greenhouse in Bleiswijk, The Netherlands. Plants were produced using conventional greenhouse production protocols for *Astroloba* which consisted of regular irrigation and fertilizer applications. No chemical pest or disease measures were utilized in production. Plants were grown under light levels of approximately 12.5 lux.

Those skilled in the art will appreciate that certain characteristics will vary with older or, conversely, with younger plants. 'OVASDINO' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'OVASDINO' and a comparison with the parent and the closest known comparator are provided below.

Plant description:

*Growth habit.*—A non-branched basal rosette, growing into a short stem.

*Plant shape.*—Globular.

*Height from soil level to top of foliar plane.*—16.9 cm.

*Plant spread.*—Average of 20.3 cm.

*Growth rate.*—Slow.

*Plant vigor.*—Low to moderate.

*Propagation.*—Type — Leaf cuttings. Time to initiate rooting — Approximately 40 days at 17 degrees Celsius. Crop time — Approximately 8 months to produce a marketable plant in a 12 cm container; 12 months for a 17 cm container.

*Disease and pest resistance or susceptibility.*—Neither resistance nor susceptibility to typical *Astroloba spiralis* pests and diseases has been observed.

*Environmental tolerances.*—Adapt to, at least, USDA Zones 10 to 12 and temperatures as high as 40 degrees Celsius; low tolerance to rain; high tolerance to wind.

Root system:

*General.*—Fine, well-branched fibrous roots.

Stems:

*Branching habit.*—Leaves in a non-branching basal rosettes with one main stem and no lateral branches.

*Main stem.*—Dimensions — 4.0 cm long and 2.7 cm in diameter. Internode length — 0.2 cm. Aspect — Near vertical. Cross-section — Round. Texture — Smooth; glabrous. Luster — Matte. Strength — Strong. Color, juvenile — Yellow-green, RHS 145C. Color, mature — Yellow-green, in between RHS 145A to 145B. Color at internodes — Yellow-green, RHS 145C.

Foliage:

*Arrangement.*—Alternate.

*Division.*—Simple.

*Attachment.*—Sessile.

*Quantity.*—Approximately 12 leaves per plant.

*Shape.*—Succulent leaves are narrow ovate.

*Dimensions.*—15.0 cm long, 5.3 cm wide, and 0.7 cm thick, on average.

*Aspect.*—Slightly concave; slightly carinate.

*Attitude.*—Upward in an average angle of approximately 37.5 degrees to the main stem; juvenile foliage is more erect than mature foliage.

*Apex.*—Acute with a soft pungent tip.

*Base.*—Decurrent.

*Margin.*—Sharply dentate with soft spines; 1 spine per cm; spines are approximately 0.3 cm tall and colored translucent green-white, nearest to RHS 157D.

*Texture, adaxial surface.*—Glabrous and lightly covered papillae, each approximately 1.5 mm high and 1.0 mm in diameter.

*Texture, abaxial surface.*—Glabrous and moderately to densely covered papillae, each approximately 1.5 mm high and 1.0 mm in diameter.

*Luster, adaxial surface.*—Glossy.

*Luster, abaxial surface.*—Moderately glossy.

*Color.*—Juvenile foliage, adaxial surface — Green, nearest to a combination of RHS 137A and 141A, and fading to yellow-green towards the base, nearest to RHS 144A. Juvenile foliage, abaxial surface — Green, nearest to a combination of RHS 137A and 141A, and fading to yellow-green towards the base, nearest to RHS 144A; leaf sparsely covered with elliptic papillae which are colored yellow-green, nearest to a combination of RHS 145B , 145C and 145D. Mature foliage, adaxial surface — In between green, RHS 139A, and yellow-green, darker than RHS 147A; leaf lightly covered with elliptic papillae, more so towards the leaf base; papillae are colored green, nearest to RHS 143C. Mature foliage, adaxial surface — In between green, RHS NN137A, and yellow-green, darker than RHS 147A, and fading lighter towards the base, nearest to RHS NN137B; leaf moderately to densely covered with elliptic papillae, generally arranged in somewhat irregular transverse rows across the leaf surface; papillae are colored green, nearest to RHS 143C.

*Venation.*—No venation is visible.

*Petiole.*—No petiole; leaves are sessile.

Inflorescence: No flowering has been observed to date.

COMPARISONS WITH THE PARENT AND CLOSEST KNOWN COMPARATOR

Plants of the new cultivar 'OVASDINO' differ from the parent an unnamed plant of, *Astroloba spiralis*, in the following characteristics described in Table 1 below.

TABLE 1

| Characteristic | 'OVASDINO' | *Astroloba spiralis* |
|---|---|---|
| Plant size. | Large than the parent. | Smaller than 'OVASDINO'. |
| Growth habit. | A large plant comprised of a single rosette of leaves, forming a short stem with time. | A compact plant comprised of numerous columnar rosettes of foliage. |
| Leaf size. | Large leaves. | Small leaves. |
| Leaf margins | Dentate with large spines. | Margins lacking spines. |
| General coloration of mature foliage. | Dark green with light green spots. | Dark green. |

TABLE 2

| Characteristic | 'OVASDINO' | 'West Jogoo' |
|---|---|---|
| Growth habit. | Comprised of a single rosette of leaves, forming a short stem with time. | Comprised of numerous columnar rosettes of foliage. |
| Leaf width. | Broader foliage. | Narrower foliage. |
| Leaf margins | Dentate with relatively large spines. | Dentate with smaller spines. |
| General coloration of mature foliage. | Dark green with light green spots. | Dark green. |
| Attitude of juvenile foliage. | Erect. | Less erect than 'OVASDINO'. |

COMPARISONS WITH THE CLOSEST KNOWN COMPARATOR

Plants of the new cultivar 'OVASDINO' differ from the commercial variety, *Astroloba spiralis* 'West Jogoo' (not patented in the United States; European Union CPVO grant EU39575), in the following characteristics described in Table 2 below.

That which is claimed is:

1. A new and distinct variety of *Astroloba spiralis* plant named 'OVASDINO', substantially as described and illustrated herein.

* * * * *